United States Patent
Pratt

(10) Patent No.: US 6,576,646 B1
(45) Date of Patent: *Jun. 10, 2003

(54) METHODS FOR TREATING COGNITIVE IMPAIRMENTS CAUSED BY TRAUMATIC BRAIN INJURIES

(75) Inventor: Raymond Pratt, Leonia, NJ (US)

(73) Assignee: Eisai Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/054,931

(22) Filed: Jan. 25, 2002

Related U.S. Application Data

(63) Continuation of application No. 09/947,087, filed on Sep. 4, 2001, now Pat. No. 6,482,838, which is a continuation of application No. PCT/US01/07027, filed on Mar. 5, 2001.
(60) Provisional application No. 60/259,226, filed on Jan. 3, 2001, provisional application No. 60/220,783, filed on Jul. 25, 2000, provisional application No. 60/197,610, filed on Apr. 18, 2000, and provisional application No. 60/186,744, filed on Mar. 3, 2000.

(51) Int. Cl.⁷ .............................................. A61K 31/445
(52) U.S. Cl. ...................................................... 514/319
(58) Field of Search .......................................... 514/319

(56) References Cited

U.S. PATENT DOCUMENTS

| 4,895,841 A | 1/1990 | Sugimoto et al. |
| 2001/0036949 A1 | 11/2001 | Coe et al. |

FOREIGN PATENT DOCUMENTS

| JP | 4-21670 | 1/1992 |
| JP | 4-187674 | 7/1992 |
| WO | 97/46527 | 12/1997 |
| WO | WO98/39000 | 9/1998 |
| WO | WO01/66096 A2 | 9/2001 |

OTHER PUBLICATIONS

Diagnostic and Statistical Manual of Mental Disorders, 4th Ed., Text Revision, American Psychiatric Association, p. 164 (2000).

*Primary Examiner*—Rebecca Cook
(74) *Attorney, Agent, or Firm*—Hale and Dorr LLP

(57) ABSTRACT

The invention describes novel methods for treating and preventing cognitive impairments caused by traumatic brain injuries by administering a therapeutically effective amount of at least one of the cholinesterase inhibitor compounds described herein. A preferred cholinestrease inhibitor for use in the methods of the invention is donepezil hydrochloride or ARICEPT®.

16 Claims, No Drawings

METHODS FOR TREATING COGNITIVE IMPAIRMENTS CAUSED BY TRAUMATIC BRAIN INJURIES

RELATED APPLICATIONS

This application is a continuation of U.S. application Ser. No. 09/947,087 filed Sep. 4, 2001, now U.S. Pat. No. 6,482,838 which is a continuation of PCT Application No. PCT/US01/07027 filed Mar. 5, 2001, which claims priority to U.S. Provisional Application No. 60/259,226 filed Jan. 3, 2001, U.S. Provisional Application No. 60/220,783 filed Jul. 25, 2000, U.S. Provisional Application No. 60/197,610 filed Apr. 18, 2000, and U.S. Provisional Application No. 60/186,744 filed Mar. 3, 2000.

FIELD OF THE INVENTION

The invention describes novel methods for treating and preventing cognitive impairments caused by traumatic brain injuries by administering a therapeutically effective amount of at least one of the cholinesterase inhibitor compounds described herein. A preferred cholinesterase inhibitor for use in the methods of the invention is donepezil hydrochloride or ARICEPT®.

BACKGROUND OF THE INVENTION

Novel cholinesterase inhibitors are described in U.S. Pat. No. 4,895,841 and WO 98/39000, the disclosures of which are incorporated by reference herein in their entirety. The cholinesterase inhibitors described in U.S. Pat. No. 4,895,841 include donepezil hydrochloride or ARICEPT®, which has proven to be a highly successful drug for the treatment of Alzheimer's disease.

There is a need in the art for new and improved treatments for other diseases, disorders, and syndromes that are characterized by symptoms of dementia and/or cognitive impairments. The invention is directed to these, as well as other, important ends.

SUMMARY OF THE INVENTION

The invention describes novel methods for treating and preventing cognitive impairments caused by traumatic brain injuries (e.g., post head trauma) by administering to a patient a therapeutically effective amount of at least one of the cholinesterase inhibitor compounds described herein.

The present invention is described in more detail below.

DETAILED DESCRIPTION OF THE INVENTION

"Patient" refers to animals, preferably mammals, more preferably humans. The term "patient" includes adults and children, and includes men and women. Children includes neonates, infants, and adolescents.

"Cognitive impairment" prefers to an acquired deficit in one or more of memory function, problem solving, orientation and/or abstraction that impinges on an individual's ability to function independently.

"Dementia" refers to a global deterioration of intellectual functioning in clear consciousness, and is characterized by one or more symptoms of disorientation, impaired memory, impaired judgment, and/or impaired intellect. The symptoms of "dementia" are generally worse than, and can encompass, the symptoms of "cognitive impairment."

"Cognitive impairments caused by traumatic brain injury" refers to cognitive impairments, as defined herein, that are associated with or caused by traumatic brain injuries, including post-head trauma and other traumas to the head, such as, for example, traumas caused by accidents and/or sports injuries. The traumatic brain injury may be a closed head injury. The closed head injury may be transient or prolonged.

"Cognitive impairments caused by traumatic brain injury" includes dementia pugilistica, which is severe brain damage caused by repeated blows to the head (e.g., from boxing). Dementia pugilistica is a chronic and progressive clinical syndrome characterized by neurological evidence of damage to pyramidal, extrapyramidal, and cerebellar systems with associated psychosis, dementia, personality change and impaired social functioning and/or prominent signs/symptoms of Parkinsonism (e.g., tremors, dysarthria, rigidity, bradykinesia, other extrapyramidal signs).

In the methods described herein, the cholinesterase inhibitors of the invention alleviate (e.g., reduce or eliminate) at least one (preferably two, three, or all) symptom of the disease, disorder or syndrome being treated. Preferably, the cholinesterase inhibitors are alleviating the symptoms of cognitive impairments and/or dementia.

As described and defined herein, the present invention is directed to novel methods for treating and preventing cognitive impairments caused by traumatic brain injuries by administering to a patient in need thereof a therapeutically effective amount of at least one cholinesterase inhibitor. The cholinesterase inhibitor may be any known in the art including, for example, donepezil, tacrine, physostigmine, rivastigmine, galantamine, citicoline, velnacrine maleate, metrifonate, heptastigmine, and the like.

In one embodiment, the cholinesterase inhibitor is a compound of formula I, a stereoisomer thereof and/or a pharmaceutically acceptable salt thereof:

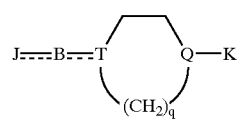

wherein J is
(a) a substituted or unsubstituted group selected from the group consisting of (1) phenyl, (2) pyridyl, (3) pyrazyl, (4) quinolyl, (5) cyclohexyl, (6) quinoxalyl, and (7) furyl;
(b) a monovalent or divalent group, in which the phenyl may have one or more substituents selected from (1) indanyl, (2) indanonyl, (3) indenyl, (4) indenonyl, (5) indanedionyl, (6) tetralonyl, (7) benzosuberonyl, (8) indanolyl, and (9) $C_6H_5$—CO—CH($CH_3$)—;
(c) a monovalent group derived from a cyclic amide compound;
(d) a lower alkyl group; or
(e) a group of $R^{21}$—CH=CH—, in which $R^{21}$ is hydrogen or a lower alkoxycarbonyl group;

B is —($CHR^{22}$)$_r$—, —CO—($CHR^{22}$)$_r$—, —$NR^4$—($CHR^{22}$)$_r$—, —CO—$NR^5$—($CHR^{22}$)$_r$—, —CH=CH—($CHR^{22}$)$_r$—, —OCOO—($CHR^{22}$)$_r$—, —OOC—NH—($CHR^{22}$)$_r$—, —NH—CO—($CHR^{22}$)$_r$—, —$CH_2$—CO—NH—($CHR^{22}$)$_r$—, —($CH_2$)$_2$—NH—($CHR^{22}$)$_r$—, —CH(OH)—($CHR^{22}$)$_r$—, =(CH—CH=CH)$_b$—, =CH—($CH_2$)$_c$—, =(CH—CH)$_d$=, —CO—CH=CH—$CH_2$—, —CO—$CH_2$—CH(OH)—$CH_2$—, —CH($CH_3$)—CO—NH—$CH_2$—, —CH=CH=CO—

NH—(CH$_2$)$_2$—, —NH—, —O—, —S—, a dialkylaminoalkylcarbonyl or a lower alkoxycarbony;

wherein R$^4$ is hydrogen, lower alkyl, acyl, lower alkylsulfonyl, phenyl, substituted phenyl, benzyl, or substituted benyl; R$^5$ is hydrogen, lower alkyl or phenyl; r is zero or an integer of about 1 to about 10; R$^{22}$ is hydrogen or methyl so that one alkylene group may have no methyl branch or one or more methyl branches; b is an integer of about 1 to about 3; c is zero or an integer of about 1 to about 9; d is zero or an integer of about 1 to about 5;

T is nitrogen or carbon;

Q is nitrogen, carbon or

q is an integer of about 1 to about 3;

K is hydrogen, phenyl, substituted phenyl, arylalkyl in which the phenyl may have a substituent, cinnamyl, a lower alkyl, pyridylmethyl, cycloalkylalkyl, adamantanemethyl, furylmenthyl, cycloalkyl, lower alkoxycarbonyl or an acyl; and ------ is a single bond or a double bond.

In the compound of formula I, J is preferably (a) or (b), more preferably (b). In the definition of (b), a monovalent group (2), (3) and (5) and a divalent group (2) are preferred. The group (b) preferably includes, for example, the groups having the formulae shown below:

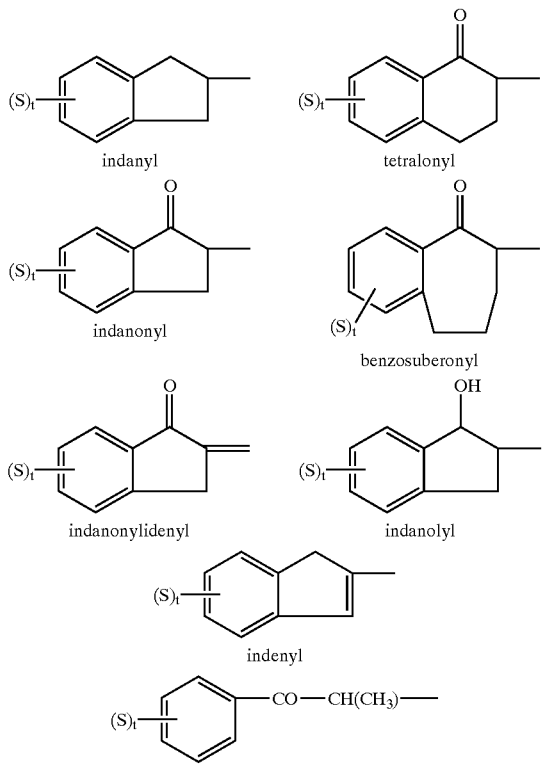

indanyl tetralonyl indanonyl benzosuberonyl indanonylidenyl indanolyl indenyl

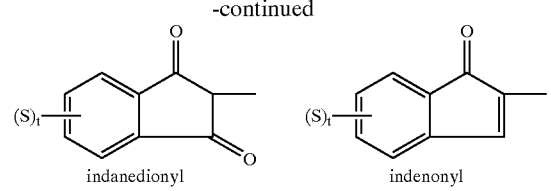

indanedionyl indenonyl wherein t is an integer of about 1 to about 4; and each S is independently hydrogen or a substituent, such as a lower alkyl having 1 to 6 carbon atoms or a lower alkoxy having 1 to 6 carbon atoms. Among the substituents, methoxy is most preferred. The phenyl is most preferred to have 1 to 3 methoxy groups thereon. (S)$_t$ may form methylene dioxy groups or ethylene dioxy groups on two adjacent carbon atoms of the phenyl group. Of the above groups, indanonyl, indanedionyl and indenyl, optionally having substituents on the phenyl, are the most preferred.

In the definition of B, —(CHR$^{22}$)$_r$—, —CO—(CHR$^{22}$)$_r$—, =(CH—CH=CH)$_b$—, =CH—(CH$_2$)$_c$— and =(CH—CH)$_d$= are preferable. The group of —(CHR$^{22}$)$_r$— in which R$^{22}$ is hydrogen and r is an integer of 1 to 3, and the group of =CH—(CH$_2$)$_c$— are most preferable. The preferable groups of B can be connected with (b) of J, in particular (b)(2).

The ring containing T and Q in formula I can be 5-, 6- or 7-membered. It is preferred that Q is nitrogen, T is carbon or nitrogen, and q is 2; or that Q is nitrogen, T is carbon, and q is 1 or 3; or that Q is carbon, T is nitrogen and q is 2.

It is preferable that K is a phenyl, arylalkyl, cinnamyl, phenylalkyl or a phenylalkyl having a substituent(s) on the phenyl.

In preferred embodiments, the cyclic amine compounds of formula I are the piperidine compounds of formula II, a stereoisomer thereof and/or a pharmaceutically acceptable salt thereof:

II

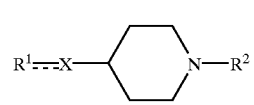

wherein R$^1$ is a (1) substituted or unsubstituted phenyl group; (2) a substituted or unsubstituted pyridyl group; (3) a substituted or unsubstituted pyrazyl group; (4) a substituted or unsubstituted quinolyl group; (5) a substituted or unsubstituted indanyl group; (6) a substituted or unsubstituted cyclohexyl group; (7) a substituted or unsubstituted quinoxalyl group; (8) a substituted or unsubstituted furyl group; (9) a monovalent or divalent group derived from an indanone having a substituted or unsubstituted phenyl ring; (10) a monovalent group derived from a cyclic amide compound; (11) a lower alkyl group; or (12) a group of the formula R$^3$—CH=C—, where R$^3$ is a hydrogen atom or a lower alkoxycarbonyl group;

X is —(CH$_2$)$_n$—, —C(O)—(CH$_2$)$_n$—, —N(R$^4$)—(CH$_2$)$_n$—, —C(O)—N(R$^5$)—(CH$_2$)$_n$—, —CH=CH—(CH$_2$)$_n$—, —O—C(O)—O—(CH$_2$)$_n$—, —O—C(O)—NH—(CH$_2$)$_n$—, —CH=CH—CH=CO—, —NH—C(O)—(CH$_2$)$_n$—, —CH$_2$—C(O)—NH—(CH$_2$)$_n$—, —(CH$_2$)$_2$—C(O)—NH—(CH$_2$)$_n$—, —CH(OH)—(CH$_2$)$_n$—, —C(O)—CH=CH—CH$_2$—, —C(O)—CH$_2$—CH(OH)—CH$_2$—, —CH(CH$_3$)—C(O)—NH—CH$_2$—, —CH=CH—C(O)—NH—(CH$_2$)$_2$—, a dialkylaminoalkylcarbonyl group, a lower alkoxycarbonyl group;

where n is an integer of 0 to 6; $R^4$ is a hydrogen atom, a lower alkyl group, an acyl group, a lower alkylsulfonyl group, a substituted or unsubstituted phenyl group, or a substituted or unsubstituted benzyl group; and $R^5$ is a hydrogen atom a lower alkyl group or a phenyl group;

$R^2$ is a substituted or unsubstituted phenyl group; a substituted or unsubstituted arylalkyl group; a cinnamyl group; a lower alkyl group; a pyridylmethyl group; a cycloalkylalkyl group; an adamantanemethyl group; or a furoylmethyl group; and ------ is a single bond or a double bond.

The term "lower alkyl group" as used herein means a straight or branched alkyl group having 1 to 6 carbon atoms. Exemplary "lower alkyl groups" include methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimthylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, and the like. The lower alkyl group is preferably methyl, ethyl, propyl or isopropyl; more preferably methyl.

Specific examples of the substituents for the substituted or unsubstituted phenyl, pyridyl, pyrazyl, quinolyl, indanyl, cyclohexyl, quinoxalyl and furyl groups in the definition of $R^1$ include lower alkyl groups having 1 to 6 carbon atoms, such as methyl, ethyl, n-propyl, isopropyl, n-butyl, isobutyl, and tert-butyl groups; lower alkoxy groups corresponding to the above-described lower alkyl groups, such as methoxy and ethoxy groups; a nitro group; halogen atoms, such as chlorine, fluorine and bromine; a carboxyl group; lower alkoxycarbonyl groups corresponding to the above-described lower alkoxy groups, such as methoxycarbonyl, ethoxycarbonyl, isopropoxycarbonyl, n-propoxycarbonyl, and n-butyloxycarbonyl groups; an amino group; a lower monoalkylamino group; a lower dialkylamino group; a carbamoyl group; acylamino groups derived from aliphatic saturated monocarboxylic acids having 1 to 6 carbon atoms, such as acetylamino, propionylamino, butyrylamino, isobutyrylamino, valerylamino, and pivaloylamino groups; cycloalkyloxycarbonyl groups, such as a cyclohexyloxycarbonyl group; lower alkylaminocarbonyl groups, such as methylaminocarbonyl and ethylaminocarbonyl groups; lower alkylcarbonyloxy groups corresponding to the above-defined lower alkyl groups, such as methylcarbonyloxy, ethylcarbonyloxy, and n-propylcarbonyloxy groups; halogenated lower alkyl groups, such as a trifluoromethyl group; a hydroxyl group; a formyl group; and lower alkoxy lower alkyl groups, such as ethoxymethyl, methoxymethyl and methoxyethyl groups. The "lower alkyl groups" and "lower alkoxyl groups" in the above description of the substituent include all the groups derived from the above-mentioned groups. The substituent may be one to three of them, which may be the same or different.

When the substituent is a phenyl group, the following group is within the scope of the substituted phenyl group:

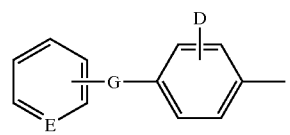

wherein G is —C(O)—, —O—C(O)—, —O—, —CH₂—NH—C(O)—, —CH₂—O—, —CH₂—SO₂—, —CH(OH)—, or —CH₂—S(→O)—; E is a carbon or nitrogen atom; and D is a substituent.

Preferred examples of the substituents (i.e., "D") for the phenyl group include lower alkyl, lower alkoxy, nitro, halogenated lower alkyl, lower alkoxycarbonyl, formyl, hydroxyl, and lower alkoxy lower alkyl groups, halogen atoms, and benzyol and benzylsulfonyl groups. The substituent may be two or more of them, which may be the same or different.

Preferred examples of the substituent for the pyridyl group include lower alkyl and amino groups and halogen atoms.

Preferred examples of the substituent for the pyrazyl group include lower alkoxycarbonyl, carboxyl, acylamino, carbamoyl, and cycloalkyloxycarbonyl groups.

With respect to $R^1$, the pyridyl group is preferably a 2-pyridyl, 3-pyridyl, or 4-pyridyl group; the pyrazyl group is preferably a 2-pyrazinyl group; the quinolyl group is preferably a 2-quinolyl or 3-quinolyl group; the quinoxalinyl group is preferably a 2-quinoxalinyl or 3-quinoxalinyl group; and the furyl group is preferably a 2-furyl group.

Specific examples of preferred monovalent or divalent groups derived from an indanone having an unsubstituted or substituted phenyl ring include those represented by formulas (A) and (B):

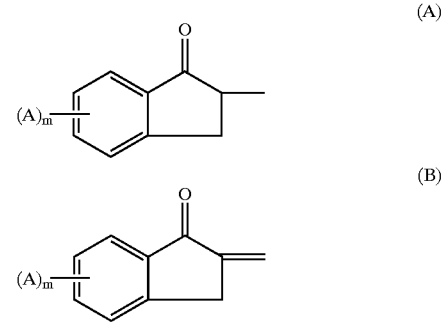

where m is an integer of from 1 to 4, and each A is independently a hydrogen atom, a lower alkyl group, a lower alkoxy group, a nitro group, a halogen atom, a carboxyl group, a lower alkoxycarbonyl group, an amino group, a lower monoalkylamino group, a lower dialkylamino group, a carbamoyl group, an acylamino group derived from aliphatic saturated monocarboxylic acids having 1 to 6 carbon atoms, a cycloalkyloxycarbonyl group, a lower alkylaminocarbonyl group, a lower alkylcarbonyloxy group, a halogenated lower alkyl group, a hydroxyl group, a formyl group, or a lower alkoxy lower alkyl group; preferably a hydrogen atom, a lower alkyl group or a lower alkoxy group; most preferably the indanone group is unsubstituted or substituted with 1 to 3 methoxy groups.

Examples of the monovalent group derived from a cyclic amide compound include quinazolone, tetrahydroisoquinolinone, tetrahydrobenzodiazepinone, and hexahydrobenzazocinone. However, the monovalent group may be any one having a cyclic amide group in the structural formula thereof, and is not limited to the above-described specific examples. The cyclic amide group may be one derived from a monocyclic or condensed heterocyclic ring. The condensed heterocyclic ring is preferably one formed by condensation with a phenyl ring. In this case, the phenyl ring may be substituted with a lower alkyl group having 1 to 6 carbon atoms, preferably a methyl group, or a lower alkoxy group having 1 to 6 carbon atoms, preferably a methoxy group.

Preferred examples of the monovalent group include the following:

(a)
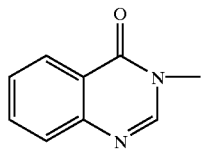

(b)
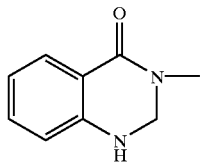

(c)
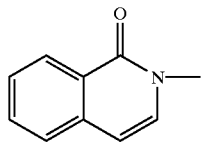

(d)
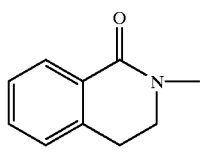

(e)
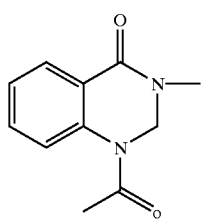

(f)
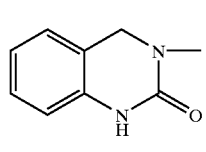

(g)
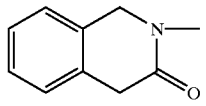

(h)
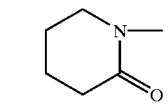

-continued (i)
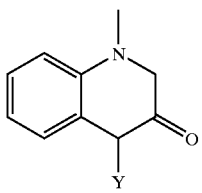

(j)
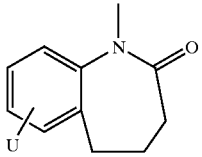

(k)
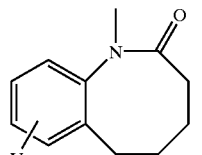

(l)
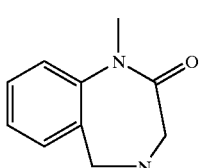

(m)
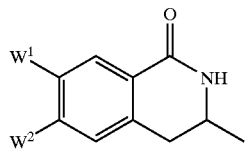

(n)
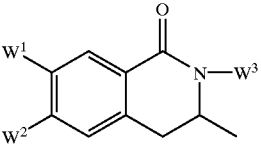

In the above formulae, Y is a hydrogen atom or a lower alkyl group; V and U are each a hydrogen atom or a lower alkoxy group (preferably dimethoxy); $W^1$ and $W^2$ are each a hydrogen atom, a lower alkyl group, or a lower alkoxy group; and $W^3$ is a hydrogen atom or a lower alkyl group. The right hand ring in formulae (j) and (l) is a 7-membered ring, while the right hand ring in formula (k) is an 8-membered ring.

The most preferred examples of the above-defined $R^1$ include a monovalent group derived from an indanone having an unsubstituted or substituted phenyl group and a monovalent group derived from a cyclic amide compound.

The most preferred examples of the above-defined X include —$(CH_2)_n$—, an amide group, or groups represented by the above formulae where n is 2. Thus, it is most preferred that any portion of a group represented by the formula $R^1$------X— have a carbonyl or amide group.

The substituents involved in the expressions "a substituted or unsubstituted phenyl group" and "a substituted or unsubstituted arylalkyl group" in the above definition of $R^2$ are the same substituents as those described for the above definitions of a phenyl group, a pyridyl group, a pyrazyl group, a quinolyl group, an indanyl group, a cyclohexyl group, a quinoxalyl group or a furyl group in the definition of $R^1$.

The term "arylalkyl group" is intended to mean an unsubstituted benzyl or phenethyl group or the like.

Specific examples of the pyridylmethyl group include 2-pyridylmethyl, 3-pyridylmethyl, and 4-pyridylmethyl groups.

Preferred examples of $R^2$ include benzyl and phenethyl groups. The symbol ------ means a double or single bond. The bond is a double bond only when $R^1$ is the divalent group (B) derived from an indanone having an unsubstituted or substituted phenyl ring, while it is a single bond in other cases.

In preferred embodiments, the compound of formula II is a compound of formula III, a stereoisomer thereof and/or a pharmaceutically acceptable salt thereof:

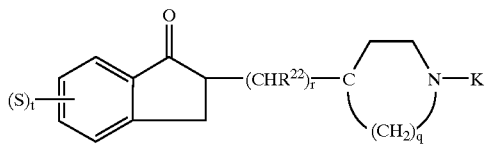

wherein r is an integer of about 1 to about 10; each $R^{22}$ is independently hydrogen or methyl; K is a phenalkyl or a phenalkyl having a substituent on the phenyl ring; each S is independently a hydrogen, a lower alkyl group having 1 to 6 carbon atoms or a lower alkoxy group having 1 to 6 carbon atoms; t is an integer of 1 to 4; q is an integer of about 1 to about 3; with the proviso that $(S)_t$ can be a methylenedioxy group or an ethylenedioxy group joined to two adjacent carbon atoms of the phenyl ring.

In preferred embodiments, the compound of formula III is 1-benzyl-4-((5,6-dimethoxy-1-indanon)-2-yl) methylpiperidine; 1-benzyl-4-((5,6-dimethoxy-1-indanon)-2-ylidenyl)methylpiperidine; 1-benzyl-4-((5-methoxy-1-indanon)-2-yl)methylpiperidine; 1-benzyl-4-((5,6-diethoxy-1-indanon)-2-yl)methylpiperidine; 1-benzyl4-((5,6-methnylenedioxy-1-indanon)-2-yl)methylpiperidine; 1-(m-nitrobenzyl)4-((5,6-dimethoxy-1-indanon)-2-yl) methylpiperidine; 1-cyclohexylmethyl-4-((5,6-dimethoxy-1-indanon)-2-yl)methylpiperidine; 1-(m-fluorobenzyl)-4-((5,6-dimethoxy-1-indanon)-2-yl)methylpiperidine; 1-benzyl-4-((5,6-dimethoxy-1-indanon)-2-yl) propylpiperidine; 1-benzyl-4-((5-isopropoxy-6-methoxy-1-indanon)-2-yl)methylpiperidine; 1-benzyl-4-((5,6-dimethoxy-1-oxoindanon)-2-yl)propenylpiperidine; stereoisomers thereof and/or pharmaceutically acceptable salts thereof.

In more preferred embodiments, the compound of formula III is 1-benzyl-4-((5,6-dimethoxy-1-indanon)-2-yl) methylpiperidine, a stereoisomer thereof and/or a pharmaceutically acceptable salt thereof. In the most preferred embodiment, the compound of formula m is 1-benzyl-4-((5, 6-dimethoxy-1-indanon)-2-yl)methylpiperidine hydrochloride or a stereoisomer thereof, which is also known as donepezil hydrochloride or ARICEPT® (Eisai Inc., Teaneck, N.J.), and which has formula (IV):

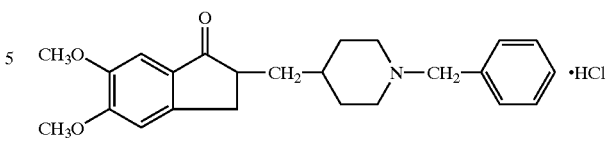

The compounds of the present invention may have an asymmetric carbon atom(s), depending upon the substituents, and can have stereoisomers, which are within the scope of the invention. For example, donepezil hydrochloride can be in the forms described in Japanese Patent Application Nos. 4-187674 and 4-21670, the disclosures of which are incorporated by reference herein in their entirety. Japanese Patent Application No. 4-187674 describes a compound having formula (V):

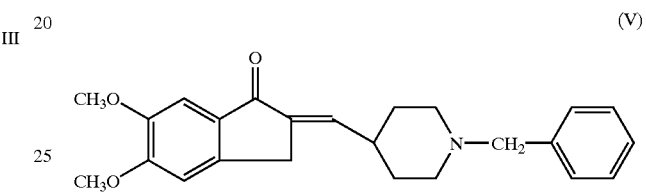

which can be in the form of a pharmaceutically acceptable salt, such as a hydrochloride salt. Japanese Patent Application No. 4-21670 describes compounds having formula (VI):

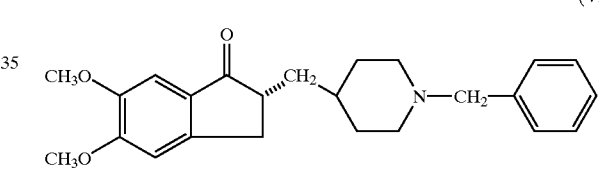

which can be in the form of a pharmaceutically acceptable salt, such as a hydrochloride salt; and compounds of formula (VII):

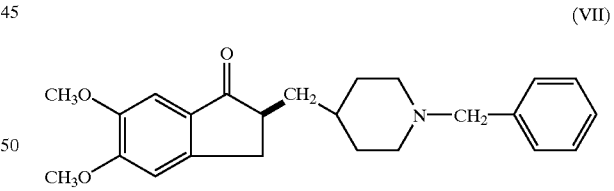

which can be in the form of a pharmaceutically acceptable salt, such as a hydrochloride salt; and compounds of formula (VIII):

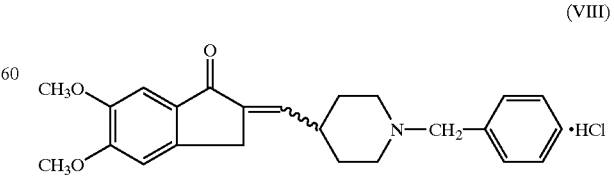

As described above, the compounds of the present invention can be administered in the form of a pharmaceutically acceptable salt. Pharmaceutically acceptable salts are known in the art and include those of inorganic acids, such as hydrochloride, sulfate, hydrobromide and phosphate; and those of organic acids, such as formate, acetate, trifluoroacetate, methanesulfonate, benzenesulfonate and toluenesulfonate. When certain substituents are selected, the compounds of the present invention may form, for example, alkali metal salts, such as sodium or potassium salts; alkaline earth metal salts, such as calcium or magnesium salts; organic amine salts, such as a salt with trimethyl-amine, triethylamine, pyridine, picoline, dicyclohexylamine or N,N'-dibenzylethylene-diamine. One skilled in the art will recognize that the compounds of the present invention can be made in the form of any other pharmaceutically acceptable salt.

The compounds of the present invention can be prepared by processes that are known in the art and described, for example, in U.S. Pat. No. 4,895,841, WO 98/39000, and Japanese Patent Application Nos. 4-187674 and 4-21670, the disclosures of each of which are incorporated by reference herein in their entirety. Donepezil hydrochloride, a preferred cholinesterase inhibitor for use in the methods described herein, is commercially available as ARICEPT® from Eisai Inc., Teaneck, N.J.

The dosage regimen for treating the diseases described herein with the cholinesterase inhibitors described herein is selected in accordance with a variety of factors, including the age, weight, sex, and medical condition of the patient, the severity of the disease, the route of administration, pharmacological considerations such as the activity, efficacy, pharmacokinetic and toxicology profiles of the particular cholinesterase inhibitor used, whether a drug delivery system is used and whether the cholinesterase inhibitor is administered as part of a drug combination.

In preferred embodiments, the cholinesterase inhibitors of the present invention are administered to treat the diseases described herein in doses of about 0.1 milligram to about 300 milligrams per day, preferably about 1 milligram to about 100 milligrams per day, more preferably about 5 milligrams to about 10 milligrams per day. The doses can be administered in one to four portions over the course of a day, preferably once a day. One skilled in the art will recognize that when the cholinesterase inhibitors of the present invention are administered to children, the dose may be smaller than the dose administered to adults, and that the dose can be dependent upon the size and weight of the patient. In preferred embodiments, a child can be administered the cholinesterase inhibitors of the present invention in doses of about 0.5 milligrams to about 10 milligrams per day, preferably about 1 milligram to about 3 milligrams per day.

In preferred embodiments of the methods described herein, a physician can administer patients donepezil hydrochloride, which is commercially available as ARICEPT® (Eisai Inc., Teaneck, N.J.), as film-coated tablets containing 5 milligrams donepezil hydrochloride or 10 milligrams donepezil hydrochloride. The tablets can be administered one to about four times a day. In preferred embodiments, one 5 milligram or one 10 milligram ARICEPT® tablet is administered once a day for the methods described herein. One skilled in the art will appreciate that when donepezil hydrochloride is administered to children, the dose may be smaller than the dose that is administered to adults. In preferred embodiments, a child can be administered donepezil hydrochloride in doses of about 0.5 milligrams to about 10 milligrams per day, preferably about 1 milligram to about 3 milligrams per day.

The cholinesterase inhibitors of the present invention can be administered orally, topically, parenterally, by inhalation (nasal or oral), or rectally in dosage unit formulations containing conventional nontoxic pharmaceutically acceptable carriers, adjuvants, and vehicles as desired. The term parenteral as used herein includes subcutaneous, intravenous, intramuscular, intrasternal injection, or infusion techniques. Preferably, the cholinesterase inhibitors of the present invention are orally administered as tablets. When administered to children, the cholinesterase inhibitors of the invention are preferably orally administered in a liquid dosage form. It will also be preferable to orally administer the cholinesterase inhibitors in a liquid dosage form to patients, such as those being treated for schizophrenia or related psychiatric disorders, who are unable to take a solid dosage form. In the methods of alleviating tobacco withdrawal syndrome described herein, the cholinesterase inhibitors can preferably be administered topically, most preferably in the form of a transdermal patch.

Injectable preparations, for example, sterile injectable aqueous or oleaginous suspensions may be formulated according to the known art using suitable dispersing or wetting agents, suspending agents (e.g., methylcellulose, Polysorbate 80, hydroxyethylcellulose, acacia, powdered tragacanth, sodium carboxymethylcellulose, polyoxytehylene sorbitan monolaurate and the like), pH modifiers, buffers, solubilizing agents (e.g., polyoxyethylene hydrogenated castor oil, Polysorbate 80, nicotinamide, polyoxyethylene sorbitan monolaurate, Macrogol, an ethyl ester of castor oil fatty acid, and the like) and preservatives. The sterile injectable preparation may also be a sterile injectable solution or suspension in a nontoxic parenterally acceptable diluent or solvent, for example, as a solution in 1,3-butanediol. Among the acceptable vehicles and solvents that may be used are water, Ringer's solution, and isotonic sodium chloride solution. In addition, sterile, fixed oils are conventionally used as a solvent or suspending medium. For this purpose any bland fixed oil may be used including synthetic mono- or diglycerides, in addition, fatty acids such as oleic acid find use in the preparation of injectables. The preparations can be lyophilized by methods known in the art.

Solid dosage forms for oral administration may include chewing gum, capsules, tablets, sublingual tablets, powders, granules and gels; most preferably tablets. In such solid dosage forms, the active compound may be admixed with one or more inert diluents such as lactose or starch. As is normal practice, such dosage forms may also comprise other substances including lubricating agents such as magnesium stearate. In the case of capsules, tablets, and pills, the dosage forms may also comprise buffering agents. The tablets can be prepared with enteric or film coatings, preferably film coatings.

In addition to the active ingredient, the tablets preferably comprise lactose monohydrate, corn starch, microcrystalline cellulose, hydroxypropyl cellulose, and magnesium stearate; while the film-coating on the tablet preferably comprises talc, polyethylene glycol, hydroxpropyl methylcellulose, titanium dioxide, and, optionally, other coloring agents, such as yellow iron oxide.

Liquid dosage forms for oral administration can include pharmaceutically acceptable emulsions, solutions, suspensions, and syrups containing inert diluents commonly used in the art, such as water. Such compositions can also comprise adjuvants, such as wetting agents, emulsifying and suspending agents, and sweetening, flavoring, and perfuming agents.

For administration by inhalation, the compositions of the invention can be delivered from an insufflator, a nebulizer or a pressured pack or other convenient mode of delivering an aerosol spray. Pressurized packs can include a suitable propellant. Alternatively, for administration by inhalation, the compositions can be administered in the form of a dry powder composition or in the form of a liquid spray.

Suppositories for rectal administration can be prepared by mixing the active compounds with suitable nonirritating excipients such as cocoa butter and polyethylene glycols that are solid at room temperature and liquid at body temperature.

For topical administration to the epidermis, the cholinesterase inhibitors can be formulated as ointments, creams or lotions, or as the active ingredient of a transdermal patch. The cholinesterase inhibitors can also be administered via iontophoresis. Ointments, creams and lotions can be formulated with an aqueous or oily base with the addition of suitable thickening and/or gelling agents. Alternatively, ointments, creams and lotions can be formulated with an aqueous or oily base and can also contain one or more emulsifying agents, stabilizing agents, dispersing agents, suspending agents, thickening agents, and/or coloring agents. As creams or lotions, the cholinesterase inhibitors can be mixed to form a smooth, homogeneous cream or lotion with, for example, one or more of a preservative (e.g., benzyl alcohol 1% or 2% (wt/wt)), emulsifying wax, glycerin, isopropyl palmitate, lactic acid, purified water, sorbitol solution. Such topically administrable compositions can contain polyethylene glycol 400. To form ointments, the cholinesterase inhibitors and/or migraine drugs can be mixed with one or more of a preservative (e.g., benzyl alcohol 2% (wt/wt)), petrolatum, emulsifying wax, and Tenox (II) (e.g., butylated hydroxyanisole, propyl gallate, citric acid, propylene glycol). Woven pads or rolls of bandaging material, e.g., gauze, can be impregnated with the transdermally administrable compositions for topical application.

The cholinesterase inhibitors can also be topically applied using a transdermal system, such as one of an acrylic-based polymer adhesive with a resinous crosslinking agent impregnated with the cholinesterase inhibitors and laminated to an impermeable backing. For example, the cholinesterase inhibitors can be administered in the form of a transdermal patch, such as a sustained-release transdermal patch. Transdermal patches can include any conventional form such as, for example, an adhesive matrix, a polymeric matrix, a reservoir patch, a matrix- or monolithic-type laminated structure, and are generally comprised of one or more backing layers, adhesives, penetration enhancers, and/or rate-controlling membranes. Transdermal patches generally have a release liner which is removed to expose the adhesive/active ingredient(s) prior to application. Transdermal patches are described in, for example, U.S. Pat. Nos. 5,262,165, 5,948,433, 6,010,715 and 6,071,531, the disclosures of which are incorporated by reference herein in their entirety.

While the cholinesterase inhibitors of the invention can be administered as the sole active pharmaceutical agent in the methods described herein, they can also be used in combination with one or more compounds which are known to be therapeutically effective against the specific disease that one is targeting for treatment.

Each of the patents and publications cited herein are incorporated by reference herein in their entirety.

It will be apparent to one skilled in the art that various modifications can be made to the invention without departing from the spirit or scope of the appended claims.

What is claimed is:

1. A method of treating one or more cognitive impairments caused by a closed head injury in a patient in need thereof comprising administering a therapeutically effective amount of a compound of formula (IV) or a pharmaceutically acceptable salt thereof:

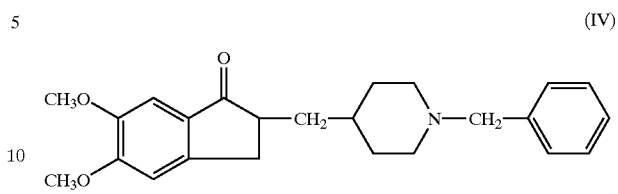

(IV)

or a stereoisomer thereof.

2. The method of claim 1, wherein the closed head injury is transient.

3. The method of claim 1, wherein the closed head injury is prolonged.

4. The method of claim 1, wherein the compound of formula (IV) is:

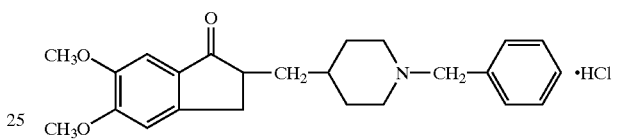

or a stereoisomer thereof.

5. The method of claim 1, wherein the compound of formula (VI) is a compound of formula (VI) or a pharmaceutically acceptable salt thereof:

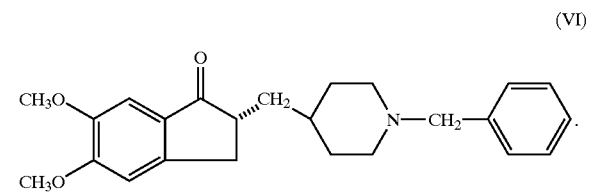

(VI)

6. The method of claim 1, wherein the compound of formula (IV) is a compound of formula (VII) or a pharmaceutically acceptable salt thereof:

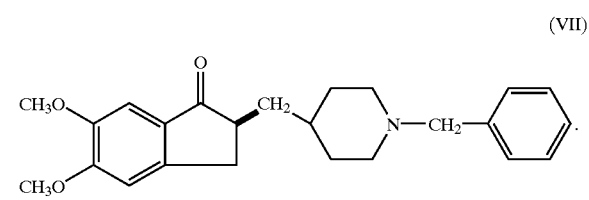

(VII)

7. The method of claim 1, wherein the compound of formula (IV), the stereoisomer thereof, or the pharmaceutically acceptable salt thereof is administered in an amount of about 1 mg to about 100 mg.

8. The method of claim 1, wherein the compound of formula (IV), the stereoisomer thereof, or the pharmaceutically acceptable salt thereof is administered in an amount of about 5 mg to about 10 mg.

9. The method of claim 1, wherein the compound of formula (IV), the stereoisomer thereof, or the pharmaceutically acceptable salt thereof is administered in an amount of about 5 milligrams.

10. The method of claim 1, wherein the compound of formula (IV), the stereoisomer thereof, or the pharmaceutically acceptable salt thereof is administered in an amount of about 10 milligrams.

11. The method of claim 1, wherein the compound of formula (IV), the stereoisomer thereof, or the pharmaceutically acceptable salt thereof is orally administered.

12. The method of claim 11, wherein the compound of formula (IV), the stereoisomer thereof, or the pharmaceutically acceptable salt thereof is orally administered in the form of a tablet.

13. The method of claim 1, wherein the compound of formula (IV), the stereoisomer thereof, or the pharmaceutically acceptable salt thereof is topically administered to the epidermis.

14. The method of claim 1, wherein the patient is a human adult.

15. The method of claim 1, wherein the patient is a human child.

16. The method of claim 1, wherein the compound of formula (IV), the stereoisomer thereof, or the pharmaceutically acceptable salt thereof is administered by nasal inhalation.

* * * * *